United States Patent [19]

Keller

[11] 4,408,360

[45] Oct. 11, 1983

[54] VARIO-HEAD ENDOPROSTHESIS

[75] Inventor: Arnold Keller, Kaihude, Fed. Rep. of Germany

[73] Assignee: Waldemar Link GmbH & Co., Hamburg, Fed. Rep. of Germany

[21] Appl. No.: 309,722

[22] Filed: Oct. 8, 1981

[30] Foreign Application Priority Data

Nov. 6, 1980 [EP] European Pat. Off. ........ 80106835.4

[51] Int. Cl.³ .............................................. A61F 1/24
[52] U.S. Cl. ................................. 3/1.913; 128/92 CA
[58] Field of Search .................................. 3/1.9–1.913; 128/92 C, 92 CA

[56] References Cited

U.S. PATENT DOCUMENTS

| 3,813,699 | 6/1974 | Giliberty | 3/1.913 |
| 3,818,512 | 6/1974 | Shersher | 3/1.912 |
| 3,848,272 | 11/1974 | Noiles | 3/1.913 |
| 3,875,593 | 4/1975 | Shersher | 3/1.912 |
| 4,044,403 | 8/1977 | D'Errico | 3/1.913 |
| 4,172,296 | 10/1979 | D'Errico | 3/1.913 X |

FOREIGN PATENT DOCUMENTS

| 2437199 | 5/1980 | France | 3/1.912 |
| 1573608 | 8/1980 | United Kingdom | 3/1.913 |

Primary Examiner—Ronald L. Frinks
Attorney, Agent, or Firm—Prutzman, Kalb, Chilton & Alix

[57] ABSTRACT

The invention relates to a vario-head endoprosthesis, consisting of a ball-shaft prosthesis (5), for example a femur prosthesis, and a vario-head socket (1, 2) which is provided with a positive safeguard for the prosthesis head, in the form of a construction of the aperture of the socket. To prevent an undesirable dislocation of the prosthesis head from the socket, the constriction is formed, according to the invention, by a ring (11) which is held in an annular groove (8) in the socket, close to the aperture. After the head has been inserted, the ring can be pushed in and withdrawn in the circumferential direction through a cut-out (10) in the groove.

6 Claims, 2 Drawing Figures

VARIO-HEAD ENDOPROSTHESIS

DESCRIPTION

The invention relates to a vario-head endoprosthesis, consisting of a ball-shaft prosthesis, for example a femur prosthesis, and a vario-head socket which is provided with a positive safeguard for the prosthesis head, in the form a constriction of the aperture of the socket.

Vario-head prostheses are mainly used for patients in cases where the socket of the hip bone is in good condition and only the head of the thigh bone needs to be replaced. Previously, so-called large-head prostheses were used in such cases, wherein the head of the femur prosthesis is shaped to fit the acetabulum; however, due to the continual relative movement, the tissue of the socket of the hip bone can be damaged by the metal head in this arrangement. For these applications, vario-head prostheses are therefore preferred in which, instead of a large femur prosthesis head, the vario-head socket is inserted into the acetabulum, this socket generally consisting of a metal shell and a plastic insert. The relative movement then takes place predominantly between the smaller head of the femur prosthesis on the one hand and the plastic insert of the vario-head socket. Sliding between the metal shell and the acetabulum can additionally occur only in the case of an extreme movement.

In known vario-head prostheses, the aperture of the socket is slightly constricted as compared with the largest diameter in order to lock the prosthesis head, and specifically it is constricted to such an extent that the prosthesis head can still just be inserted into the socket, with an elastic deformation of the socket. It is the object of the invention to provide a safeguard against luxation, which goes beyond the action of this known constriction.

The object according to the invention is achieved when the constriction of the aperture of the vario-head socket is formed by a ring which can be inserted into an annular groove formed in the aperture region of the socket, and the collar which delimits the annular groove on the aperture side of the socket is cut out at one point to enable the split ring to be inserted or withdrawn in the circumferential direction.

Regardless of the maximum diameter of the prosthesis head, this ring can be sized such that luxation is generally precluded.

Expediently, a point for applying a withdrawal tool is provided on at least one end of the split ring, and this advantageously has the form of a hole. It has also proved to be appropriate for the ring to be grooved at least on its side which is intended to face outwards, so that it can be displaced in the circumferential direction when it is to be taken out and the end of the split ring is not located in the cut-cut.

Although the ring according to the invention forms an adequate safeguard against luxation, it is possible additionally also to provide the constriction, which was mentioned at the outset, and which is in itself known, of the socket in the aperture region. On the one hand, this relieves the ring and, on the other hand, results in more secure holding of the ring, since the latter can be held within the socket diameter which is smaller than that which would be required in the absence of the said constriction.

The invention is not restricted to use in the case of hip joint prostheses. Rather, its principle can also be applied to other ball-and-socket joints or similar ball joints, for example in the case of the shoulder joint, the wrist, and finger joints and toe joints.

In the text which follows, the invention is explained in more detail by reference to the drawing in which.

Figure 1:
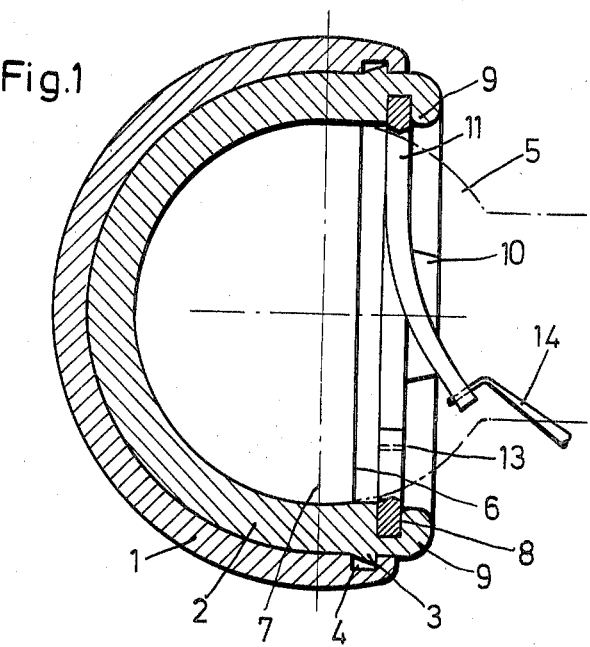
FIG. 1 shows a longitudinal section.
Figure 2:
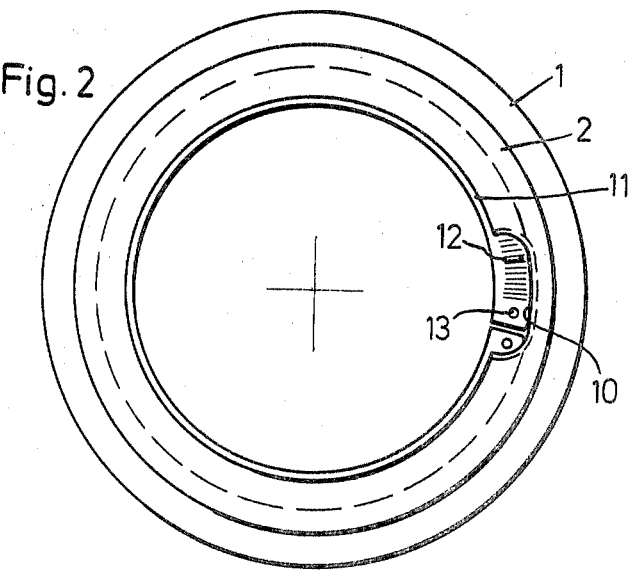
FIG. 2 shows a plan view of the aperture side of the socket according to the invention.

The socket consists of a metal shell 1 and a plastic insert 2 which preferably is composed of high-molecular low-pressure polyethylene and which is secured in an annular groove 4 of the metal shell by means of a ring nose 3. The socket surrounds the prosthesis head 5, indicated in dots and dashes, for more than 90°, namely up to the diameter 6 which is slightly smaller than the maximum diameter at 7. To this extent, the arrangement can be regarded as known.

On the aperture side of the diameter 6, the internal surface of the socket has an essentially cylindrical shape with a recessed annular groove 8 which is bounded by two parallel planes perpendicular to the axis of rotation. The collar 9 which delimits the groove 8 on the aperture side has a cut-out 10 which extends over the full radial depth of the groove and, in the circumferential direction, has a length which approximately corresponds to three to six times the width of the groove in the axial direction. In the groove, the split ring 11 is seated, the outer surface of which is grooved, as shown at 12, and the ends of the split ring contain small holes 13 in the axial direction, into which the tip of a hooked tool 14 can be inserted. In the normal state, the ring is completely contained within the groove 10. Its inward radial extent is such that it comes close to the surface of the prosthesis head 5, except for the usual tolerance. On its radially inward surface it is chamfered on both sides in the shape of a roof, so that it can be inserted independently of direction, either one or the other chamfered surface interacting with the surface of the head. As shown in FIG. 1, the ring can be introduced into the groove, or withdrawn from the latter, through the cut-out 10 with corresponding bending. When it is to be withdrawn, it is initially rotated in the circumferential direction with the aid of the tool on the grooving 12 in such a way that the end of the split ring which is to be withdrawn is located in the cut-out 10. Subsequently, this end of the split ring can be bent out of the cut-out 10 and withdrawn by means of the tool 14 engaging in the appropriate hole.

The ring 11 is securely held in the groove 8, since the latter has a depth which is considerable by comparison with the radial extent of the ring and which advantageously is larger than half the radial extent of the ring.

Advantageously, the ring 11 consists of the same material as the socket insert 2. Its diameter in the untensioned state can be greater than the diameter of the bottom of the groove 8, so that it is held more securely in the groove.

I claim:

1. A vario-head endoprosthesis comprising a ball-shaft prosthesis, for example a femur prosthesis, and a vario-head prosthesis having an outer shell and an inner insert which provides a socket for the prosthesis ball having an aperture forming a constriction providing a positive safeguard against removal of the prosthesis ball from the socket, characterized in that the insert has a collar with an inwardly facing annular groove (8) surrounding and opening into the aperture region of the socket (1,2), and the constriction is formed by a split ring (11) mounted within the annular groove and retained therein against expansion to engage and positively retain the prosthesis ball within the socket, the split ring being flexible so as to be adapted to be inserted circumferentially into the annular groove (8) and the opening side of the socket collar having cut-out means (10) to enable the split ring (11) to be inserted into or withdrawn from the annular groove in the circumferential direction.

2. Vario-head endoprosthesis according to claim 1, characterised in that a means for applying a withdrawal tool (14) is formed on at least one end of the split ring (11).

3. Vario-head endoprosthesis according to claim 2, characterised in that both ends of the split ring have a hole (13).

4. Vario-head endoprosthesis according to claim 1, charcterised in that, in the aperture region, the insert additionally has a constriction (6) which elastically yields on insertion of the prosthesis ball.

5. A vario-head endoprosthesis comprising a ball-shaft prosthesis, for example a femur prosthesis, and a vario-head socket having an aperture forming a constriction providing a positive safeguard against removal of the prosthesis ball from the socket, characterized in that the vario-head socket has a collar which delimits an inwardly facing annular groove (8) surrounding the aperture region of the socket (1, 2), and the constriction is formed by a split ring (11) adapted to be inserted circumferentially into the annular groove (8) and the opening side of the socket collar has cut-out means (10) to enable the split ring (11) to be inserted into or withdrawn from the annular groove in the circumferential direction, the split ring (11) having grooves (12) at least on its side intended to face outwardly for aiding circumferential displacement of the ring (11) within said annular groove (8).

6. A vario-head endoprosthesis comprising a ball-shaft prosthesis, for example a femur prosthesis, and a vario-head socket having an aperture forming a constriction providing a positive safeguard against removal of the prosthesis ball from the socket, characterized in that the vario-head socket has a collar which delimits an inwardly facing annular groove (8) surrounding the aperture region of the socket (1, 2), and the constriction is formed by a split ring (11) adapted to be inserted circumferentially into the annular groove (8) and the opening side of the socket collar has cut-out means (10) to enable the split ring (11) to be inserted into or withdrawn from the annular groove in the circumferential direction, the split ring (11) having means formed on at least one end thereof for applying a withdrawal tool (14) for withdrawing the split ring (11) from the said annular groove (8), and the split ring (11) having grooves (12) on at least its one side which is intended to face outwardly for aiding circumferential displacement of the split ring (11) within said annular groove (8).

* * * * *